(12) United States Patent
Gaidar et al.

(10) Patent No.: US 10,368,112 B2
(45) Date of Patent: Jul. 30, 2019

(54) TECHNOLOGIES FOR IMMERSIVE USER SENSORY EXPERIENCE SHARING

(71) Applicant: Intel Corporation, Santa Clara, CA (US)

(72) Inventors: Tamara Gaidar, Haifa (IL); Patrick J. Neschleba, Mountain View, CA (US); Richard T. Beckwith, Hillsboro, OR (US); Yosi Govezensky, Nofit (IL); Amit Moran, Tel Aviv (IL)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/998,271

(22) Filed: Dec. 26, 2015

(65) Prior Publication Data

US 2017/0188066 A1  Jun. 29, 2017

(51) Int. Cl.
  *H04H 60/33* (2008.01)
  *H04N 21/25* (2011.01)
  (Continued)

(52) U.S. Cl.
  CPC ............ *H04N 21/252* (2013.01); *A61L 9/015* (2013.01); *G06F 3/011* (2013.01); *G06F 3/016* (2013.01); *G06F 3/14* (2013.01); *H04N 21/2187* (2013.01); *H04N 21/25891* (2013.01); *H04N 21/42201* (2013.01); *H04N 21/44218* (2013.01); *H04N 21/4788* (2013.01); *H04N 21/8133* (2013.01); *A61L 2209/111* (2013.01); *G06F 3/015* (2013.01); *G06F 3/017* (2013.01); *G06F 3/03547* (2013.01); *G06F 2203/011* (2013.01); *G09G 2370/02* (2013.01); *G09G 2370/20* (2013.01)

(58) Field of Classification Search
  CPC ........ H04N 21/252; G06F 3/015; G06F 3/016
  See application file for complete search history.

(56) References Cited

U.S. PATENT DOCUMENTS

2002/0044203 A1   4/2002  Sapir
2010/0205541 A1*  8/2010  Rapaport ............... G06Q 10/10
                                                 715/753
(Continued)

OTHER PUBLICATIONS

International search report for PCT application No. PCT/US2016/063605, dated Mar. 16, 2017 (3 pages).
(Continued)

*Primary Examiner* — Olugbenga O Idowu
(74) *Attorney, Agent, or Firm* — Barnes & Thornburg LLP (57) ABSTRACT

Technologies for immersive sensory experience sharing include one or more experience computing devices, an experience server, and a distance computing device. Each experience computing device captures sensor data indicative of a local sensory experience from one or more sensors and transmits the sensor data to the experience server. Sensors may include audiovisual sensors, touch sensors, and chemical sensors. The experience server analyzes the sensor data to generate combined sensory experience data and transmits the combined sensory experience data to the distance computing device. The experience server may identify one or more activities associated with the local sensory experience. The distance computing device renders a sensory experience based on the combined sensory experience data. The distance computing device may monitor a user response, generate user preferences based on the user response, and transmit the user preferences to the experience server. Other embodiments are described and claimed.

16 Claims, 5 Drawing Sheets

(51) Int. Cl.
*G06F 3/14* (2006.01)
*G06F 3/01* (2006.01)
*H04N 21/442* (2011.01)
*H04N 21/258* (2011.01)
*H04N 21/81* (2011.01)
*H04N 21/2187* (2011.01)
*H04N 21/422* (2011.01)
*H04N 21/4788* (2011.01)
*A61L 9/015* (2006.01)
*G06F 3/0354* (2013.01)

(56) References Cited

U.S. PATENT DOCUMENTS

| | | | |
|---|---|---|---|
| 2011/0095916 A1 | 4/2011 | Kass et al. | |
| 2012/0324494 A1* | 12/2012 | Burger | H04H 60/33 |
| | | | 725/12 |
| 2013/0031590 A1* | 1/2013 | Ivanov | H04N 21/4524 |
| | | | 725/110 |
| 2013/0046847 A1* | 2/2013 | Zavesky | H04W 4/70 |
| | | | 709/217 |
| 2014/0073245 A1 | 3/2014 | Frantz | |
| 2014/0115092 A1* | 4/2014 | Tofighbakhsh | H04L 67/22 |
| | | | 709/217 |
| 2015/0012132 A1 | 1/2015 | Francis, Jr. et al. | |
| 2015/0061845 A1 | 3/2015 | Phillips et al. | |

OTHER PUBLICATIONS

Written opinion for PCT application No. PCT/US2016/063605, dated Mar. 16, 2017 (8 pages).

\* cited by examiner

TECHNOLOGIES FOR IMMERSIVE USER SENSORY EXPERIENCE SHARING

BACKGROUND

Many persons may wish to experience a public event such as a concert, show, sporting event, meeting, or other event that they are unable to attend in person. Current technologies for experiencing a distant event include watching a television broadcast or otherwise consuming broadcast media coverage of the event. Certain pre-recorded media including short films may provide additional media experiences beyond typical audiovisual playback, such as motion effects or environmental effects like mist or fog. However, such additional media experiences are typically only available by attending purpose-built theaters or other installations, such as those found at theme parks.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 1:
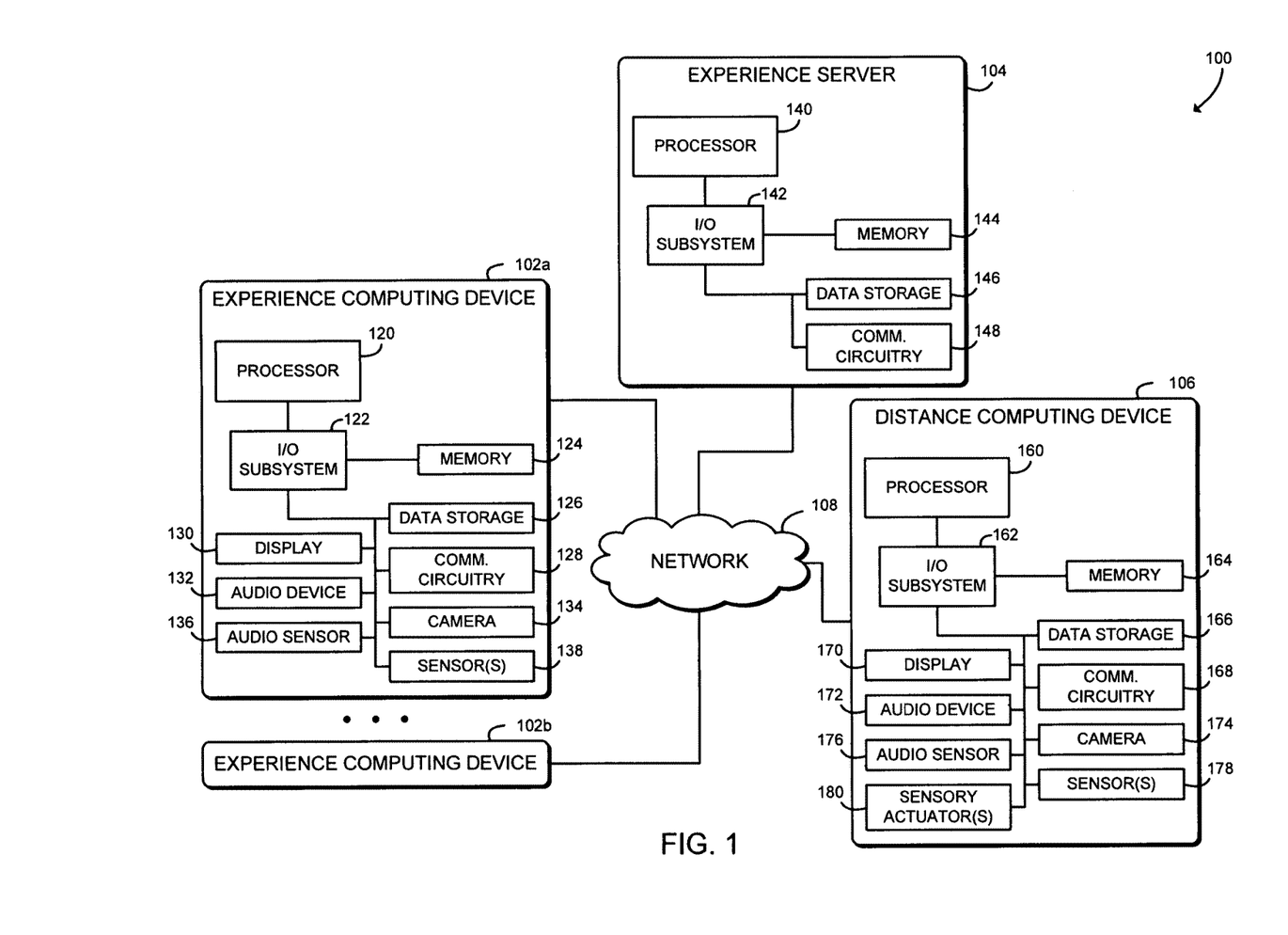
FIG. 1 is a simplified block diagram of at least one embodiment of a system for immersive sensory experience sharing.

Referring now to FIG. 1, in an illustrative embodiment, a system 100 for immersive sensory experience sharing includes one or more experience computing devices 102, an experience server 104, and a distance computing device 106 in communication over a network 108. In use, as described in more detail below, a user of the distance computing device 106 may request one or more experience computing devices 102 to share the local sensory experiences of the experience computing device 102. If the request is accepted, the experience computing devices 102 capture sensor data indicative of a local sensory experience (e.g., indicative of the point of view of a local, experience user) and transmit the sensor data to the central experience server 104. The experience server 104 analyzes and combines the sensor data and transmits combined sensory experience data to the distance computing device 106. The distance computing device 106 generates a sensory experience based on the combined sensory experience data. The distance computing device 106 may be distant from the experience computing devices 102 in space and/or time. Thus, the system 100 may allow the distance user to share an experience (e.g., a concert, show, meeting, or other public event) with other persons at the event (e.g., with the distance user's friends who are able to attend). The distance user may see what the other persons see, hear what they hear, and feel what they feel. Accordingly, the system 100 may improve experiences for persons physically unable to attend an event. Additionally, the system 100 may allow the distance user to have a dynamic sensory experience that is not prerecorded and adapts to the event. Thus, in some embodiments, by allowing the sensory experience to be shared, the system 100 may facilitate non-verbal communication between experience users and the distance user. In some embodiments, the system 100 may monitor the distance user's reactions to determine the distance user's preferences and modify the rendered sensory experience based on the preferences of the distance user.

The experience computing device 102 may be embodied as any type of computation or computer device capable of performing the functions described herein, including, without limitation, a mobile computing device, a wearable computing device, a computer, a laptop computer, a notebook computer, a tablet computer, an unmanned aerial vehicle, a network appliance, a web appliance, a distributed computing system, a processor-based system, and/or a consumer electronic device. As shown in FIG. 1, each experience computing device 102 illustratively includes a processor 120, an input/output subsystem 122, a memory 124, a data storage device 126, and communication circuitry 128. Of course, the experience computing device 102 may include other or additional components, such as those commonly found in a server (e.g., various input/output devices), in other embodiments. Additionally, in some embodiments, one or more of the illustrative components may be incorporated in, or otherwise form a portion of, another component. For example, the memory 124, or portions thereof, may be incorporated in the processor 120 in some embodiments.

The processor 120 may be embodied as any type of processor capable of performing the functions described herein. The processor 120 may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the experience computing device 102 such as operating systems, applications, programs, libraries, and drivers. The memory 124 is communicatively coupled to the processor 120 via the I/O subsystem 122, which may be embodied as circuitry and/or components to facilitate input/output operations with the processor 1'20, the memory 124, and other components of the experience computing device 102. For example, the I/O subsystem 122 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 122 may form a portion of a system-on-a-chip (SoC) and be incorporated, along with the processors 120, the memory 124, and other components of the experience computing device 102, on a single integrated circuit chip.

The data storage device 126 may be embodied as any type of device or devices configured for short-term or long-term storage of data such as, for example, memory devices and circuits, memory cards, hard disk drives, solid-state drives, or other data storage devices. As described further below, the data storage device 126 may store and/or index various media objects and associated context data.

The communication circuitry 128 of the experience computing device 102 may be embodied as any communication circuit, device, or collection thereof, capable of enabling communications between the experience computing device 102, the experience server 104, the distance computing device 106, and/or other remote devices over the network 108. The communication circuitry 128 may be configured to use any one or more communication technology (e.g., wired or wireless communications) and associated protocols (e.g., Ethernet, Bluetooth®, Wi-Fi®, WiMAX, etc.) to effect such communication.

Each experience computing device 102 may also include a display 130 and an audio device 132, as well as a camera 134, an audio sensor 136, and one or more sensors 138. The display 130 may be embodied as any type of display capable of displaying digital information such as a liquid crystal display (LCD), a light emitting diode (LED), a plasma display, a cathode ray tube (CRT), or other type of display device. In some embodiments, the display 130 may be embodied as a head-mounted display, heads-up display, or other display configured to display visual data in the user's field of vision. The audio device 132 may be embodied as any device capable of generating audio signals for output, such as a paper cone speaker, an audio transducer, a line out jack, a digital-to-analog converter (DAC), or other type of audio device.

The camera 134 may be embodied as a digital camera or other digital imaging device integrated with the experience computing device 102 or otherwise communicatively coupled thereto. The camera 134 includes an electronic image sensor, such as an active-pixel sensor (APS), e.g., a complementary metal-oxide-semiconductor (CMOS) sensor, or a charge-coupled device (CCD). The camera 134 may be used to capture images of the environment and/or user of the experience computing device 102 including, in some embodiments, capturing still images or video images. Similarly, the audio sensor 136 may be embodied as any sensor capable of capturing audio signals such as one or more microphones, a line input jack and associated circuitry, an analog-to-digital converter (ADC), or other type of audio sensor. The audio sensor 136 may be used to detect the audio environment of the experience computing device 102.

The sensors 138 may include any sensors capable of measuring or otherwise capturing data indicative of the environment of the experience computing device 102. The sensors 138 may include a chemical sensor capable of detecting scents in the environment, a motion sensor, a temperature sensor, a touch and/or pressure sensor, a biometric sensor (e.g., a heart rate sensor, a galvanic skin response sensor, or other biometric sensor), and/or other sensors. In some embodiments, the sensors 138 may be in contact with or otherwise capable of sensing a user of the experience computing device 102. For example, one or more of the sensors 138 may be integrated into a garment or other wearable device. Each experience computing device 102 may also include any number of additional input/output devices, interface devices, and/or other peripheral devices. For example, in some embodiments, the peripheral devices may include a touch screen, graphics circuitry, keyboard, mouse, speaker system, network interface, and/or other input/output devices, interface devices, and/or peripheral devices.

The experience server 104 may be embodied as any type of computation or computer device capable of performing the functions described herein, including, without limitation, a computer, a multiprocessor system, a server, a rack-mounted server, a blade server, a laptop computer, a notebook computer, a tablet computer, a wearable computing device, a network appliance, a web appliance, a distributed computing system, a processor-based system, and/or a consumer electronic device. Thus, the experience server 104 includes components and devices commonly found in a server or similar computing device, such as a processor 140, an I/O subsystem 142, a memory 144, a data storage device 146, communication circuitry 148, and/or other peripheral devices. Those individual components of the experience server 104 may be similar to the corresponding components of the experience computing device 102, the description of which is applicable to the corresponding components of the experience server 104 and is not repeated herein so as not to obscure the present disclosure. Additionally, in some embodiments, the experience server 104 may be embodied as a "virtual server" formed from multiple computing devices distributed across the network 108 and operating in a public or private cloud. Accordingly, although the experience server 104 is illustrated in FIG. 1 as embodied as a single server computing device, it should be appreciated that the experience server 104 may be embodied as multiple devices cooperating together to facilitate the functionality described below.

Similarly, the distance computing device 106 may be embodied as any type of computation or computer device capable of performing the functions described herein, including, without limitation, a smartphone, a computer, a desktop computer, a workstation, a laptop computer, a notebook computer, a tablet computer, a wearable computing device, a network appliance, a web appliance, a server, a distributed computing system, a processor-based system, and/or a consumer electronic device. The distance computing device 106 may include components and devices commonly found in a smartphone or similar computing device, such as a processor 160, an I/O subsystem 162, a memory 164, a data storage device 166, communication circuitry 168, and/or other peripheral devices. The distance computing device 106 may also include components and devices similar to those of an experience computing device 102, such as a display 170, an audio device 172, a camera 174, an audio sensor 176, and additional sensors 178. Those individual components of the distance computing device 106 may be similar to the corresponding components of the experience computing device 102 and/or the experience server 104, the description of which is applicable to the corresponding components of the distance computing device 106 and is not repeated herein so as not to obscure the present disclosure.

As shown, the distance computing device 106 may also include additional sensory actuators 180. Each sensor actuator 180 may be embodied as any component configured to generate a sensory phenomenon for a user of the distance computing device 106. For example, the sensory actuators 180 may include as a haptic feedback unit, a force feedback unit, and/or any other device that generates a sensation of touch and/or pressure for the user. As another example, the sensory actuators 180 may include a device that emits chemicals to generate a scent for the user. As yet another example, the sensory actuators 180 may include a device that generates a hot or cold sensation. The sensory actuators 180 may be distributed or otherwise included in separate system elements. For example, in some embodiments, one or more of the sensory actuators 180 may be incorporated in a wearable device such as a garment, smart watch, or smart band.

As discussed in more detail below, the experience computing devices 102, the experience server 104, and the distance computing device 106 may be configured to transmit and receive data with each other and/or other devices of the system 100 over the network 108. The network 108 may be embodied as any number of various wired and/or wireless networks. For example, the network 108 may be embodied as, or otherwise include, a wired or wireless local area network (LAN), a wired or wireless wide area network (WAN), a cellular network, and/or a publicly-accessible, global network such as the Internet. As such, the network 108 may include any number of additional devices, such as additional computers, routers, and switches, to facilitate communications among the devices of the system 100.

Additionally, although the system 100 is illustrated as including the experience computing devices 102, the experience server 104, and the distance computing device 106, it should be understood that some or all of the functions of those devices may be combined into a single device. For example, some or all of the functions of the experience server 104 may be performed by one or more of the experience computing devices 102 and/or the distance computing device 106.

Figure 2:
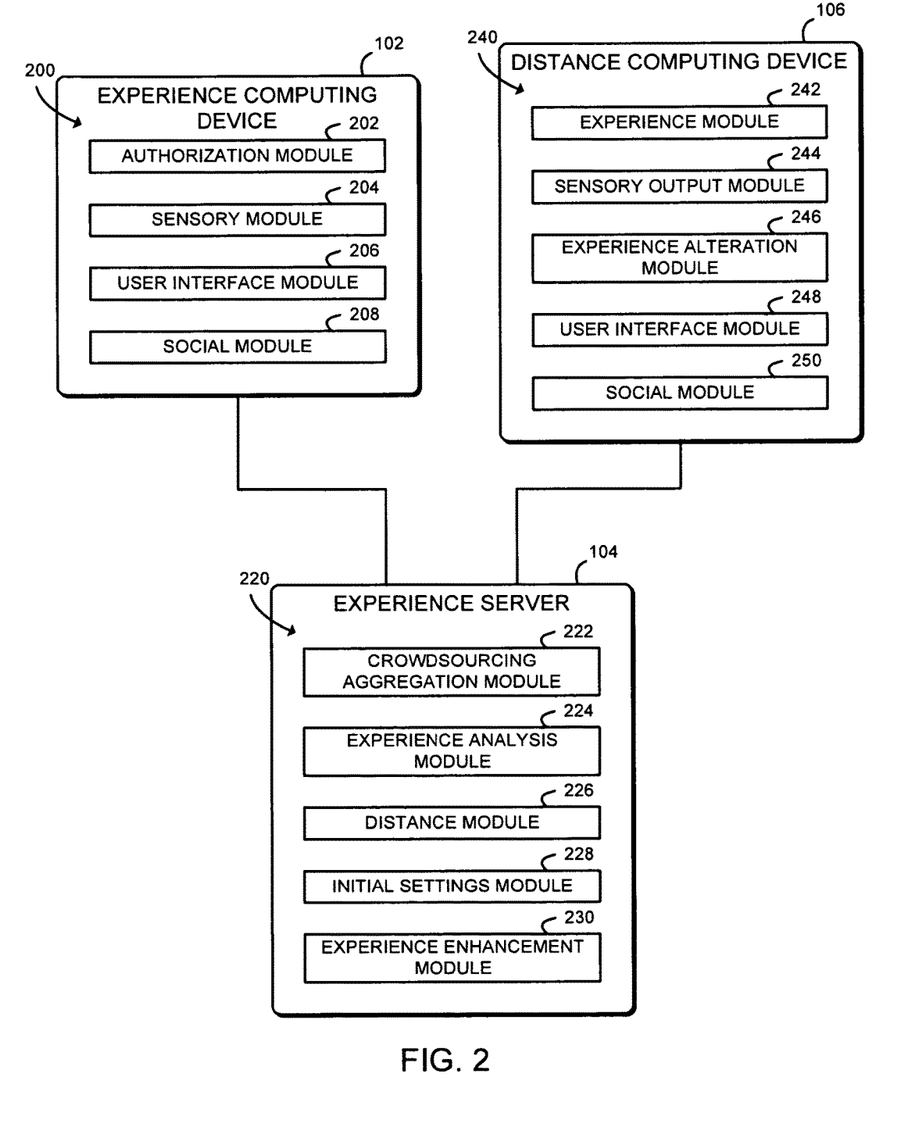
FIG. 2 is a simplified block diagram of at least one embodiment of various environments that may be established by the system of FIG. 1.

Referring now to FIG. 2, in an illustrative embodiment, an experience computing device 102 establishes an environment 200 during operation. The illustrative environment 200 includes an authorization module 202, a sensory module 204, a user interface module 206, and a social module 208. The various modules of the environment 200 may be embodied as hardware, firmware, software, or a combination thereof. As such, in some embodiments, one or more of the modules of the environment 200 may be embodied as circuitry or collection of electrical devices (e.g., authorization circuitry 202, sensory circuitry 204, user interface circuitry 206, and/or social circuitry 208). It should be appreciated that, in such embodiments, one or more of the authorization circuitry 202, the sensory circuitry 204, the user interface circuitry 206, and/or the social circuitry 208 may form a portion of one or more of the processor 120, the I/O subsystem 122, and/or other components of the experience computing device 102. Additionally, in some embodiments, one or more of the illustrative modules may form a portion of another module and/or one or more of the illustrative modules may be independent of one another.

The authorization module 202 is configured to receive a request to share a local sensory experience. The authorization module 202 is further configured to receive approval from a user of the experience computing device 102 to share the local sensory experience. The sensory module 204 is configured to capture sensor data indicative of the local sensory experience from one or more of the camera 134, the audio sensor 136, and/or the sensors 138 in response to receiving approval from the user. The sensory module 204 is further configured to transmit the sensor data to the experience server 104.

The user interface module 206 is configured to communicate with the distance computing device 106 that is sharing the local sensory experience with the experience computing device 102. Communication may include exchanging text messages, audio messages, and/or video messages. In some embodiments communication may include inviting the distance computing device 106 to receive additional sensor data indicative of the local sensory experience. The social module 208 is configured to publish the sensor data indicative of the local sensory experience to a social media server.

Still referring to FIG. 2, in the illustrative embodiment, the experience server 104 establishes an environment 220 during operation. The illustrative environment 220 includes a crowdsourcing aggregation module 222, an experience analysis module 224, a distance module 226, an initial settings module 228, and an experience enhancement module 230. The various modules of the environment 220 may be embodied as hardware, firmware, software, or a combination thereof. As such, in some embodiments, one or more of the modules of the environment 220 may be embodied as circuitry or collection of electrical devices (e.g., crowdsourcing aggregation circuitry 222, experience analysis circuitry 224, distance circuitry 226, initial settings circuitry 228, and/or experience enhancement circuitry 230). It should be appreciated that, in such embodiments, one or more of the crowdsourcing aggregation circuitry 222, the experience analysis circuitry 224, the distance circuitry 226, the initial settings circuitry 228, and/or the experience enhancement circuitry 230 may form a portion of one or more of the processor 140, the I/O subsystem 142, and/or other components of the experience server 104. Additionally, in some embodiments, one or more of the illustrative modules may form a portion of another module and/or one or more of the illustrative modules may be independent of one another.

The crowdsourcing aggregation module 222 is configured to receive sensor data from multiple experience computing devices 102. As described above, the sensor data is indicative of a local sensory experience associated with each experience computing device 102. The experience analysis module 224 is configured to analyze the sensor data to generate combined sensory experience data. The combined sensory experience data is indicative of the local sensory experiences associated with the experience computing devices 102. Analyzing the sensor data may include identifying an activity associated with the local sensory experiences based on the sensor data.

The distance module 226 is configured to transmit the combined sensory experience data to a distance computing device 106. The distance computing device 106 is distant from the experience computing devices 102. The distance module 226 may be further configured to adjust the combined sensory experience data based on user preferences associated with a user of the distance computing device 106. In some embodiments, the distance module 226 may be configured to receive the user preferences from the distance computing device 106. The initial settings module 228 is configured to initialize the user preferences based on a profile of the user of the distance computing device 106.

The experience enhancement module 230 is configured to receive an invitation from an experience computing device 102 to receive additional sensor data indicative of the local sensory experience. The experience server 104 may enhance sensor data received from the experience computing device 102 in response to receiving the invitation from the first experience device.

Still referring to FIG. 2, in the illustrative embodiment, the distance computing device 106 establishes an environment 240 during operation. The illustrative environment 240 includes an experience module 242, a sensory output module 244, an experience alteration module 246, a user interface module 248, and a social module 250. The various modules of the environment 240 may be embodied as hardware, firmware, software, or a combination thereof. As such, in some embodiments, one or more of the modules of the environment 240 may be embodied as circuitry or collection of electrical devices (e.g., experience circuitry 242, sensory output circuitry 244, experience alteration circuitry 246, user interface circuitry 248, and/or social circuitry 250). It should be appreciated that, in such embodiments, one or more of the experience circuitry 242, the sensory output circuitry 244, the experience alteration circuitry 246, the user interface circuitry 248, and/or the social circuitry 250 may form a portion of one or more of the processor 160, the I/O subsystem 162, and/or other components of the distance computing device 106. Additionally, in some embodiments, one or more of the illustrative modules may form a portion of another module and/or one or more of the illustrative modules may be independent of one another.

The experience module 242 is configured to receive combined sensory experience data from the experience server 104. As described above, the combined sensory experience data is indicative of a local sensory experience associated with each of multiple experience computing devices 102 that are distant from the distance computing device 106. The experience module 242 may be further configured to transmit a request to share the local sensory experience to the experience server 104.

The sensory output module 244 is configured to render a sensory experience based on the combined sensory experience data. For example, the sensory output module 244 may be configured to render visual data or audio data or to generate a sensory phenomenon with one or more sensory actuators 180 of the distance computing device 106. The experience alteration module 246 is configured to monitor sensor data indicative of a user response of a local user of the distance computing device 106 in response to rendering the sensory experience. The experience alteration module 246 may be further configured to generate user preferences based on the sensor data and transmit the user preferences to the experience server 104.

The user interface module 248 is configured to communicate with one or more of the experience computing devices 102. Communication may include exchanging text messages, audio messages, and/or video messages. In some embodiments, communication may include transmitting a request to control sensory input of an experience computing device 102. The social module 250 is configured to publish the sensor data indicative of the local sensory experience to a social media server.

Although the environments 200, 240 are illustrated as being established by the experience computing device 102 and the distance computing device 106, respectively, it should be understood that in some embodiments some or all of the functions of the distance computing device 106 may also be performed by an experience computing device 102, and vice versa. For example, in some embodiments, the experience computing device 102 may include a sensory output module 244 to generate an active user interface and/or an experience alteration module 246 to alter the sensory experience. In those embodiments, the experience computing device 102 may also include sensors and/or sensory actuators 180 similar to the distance computing device 106.

Figure 3:
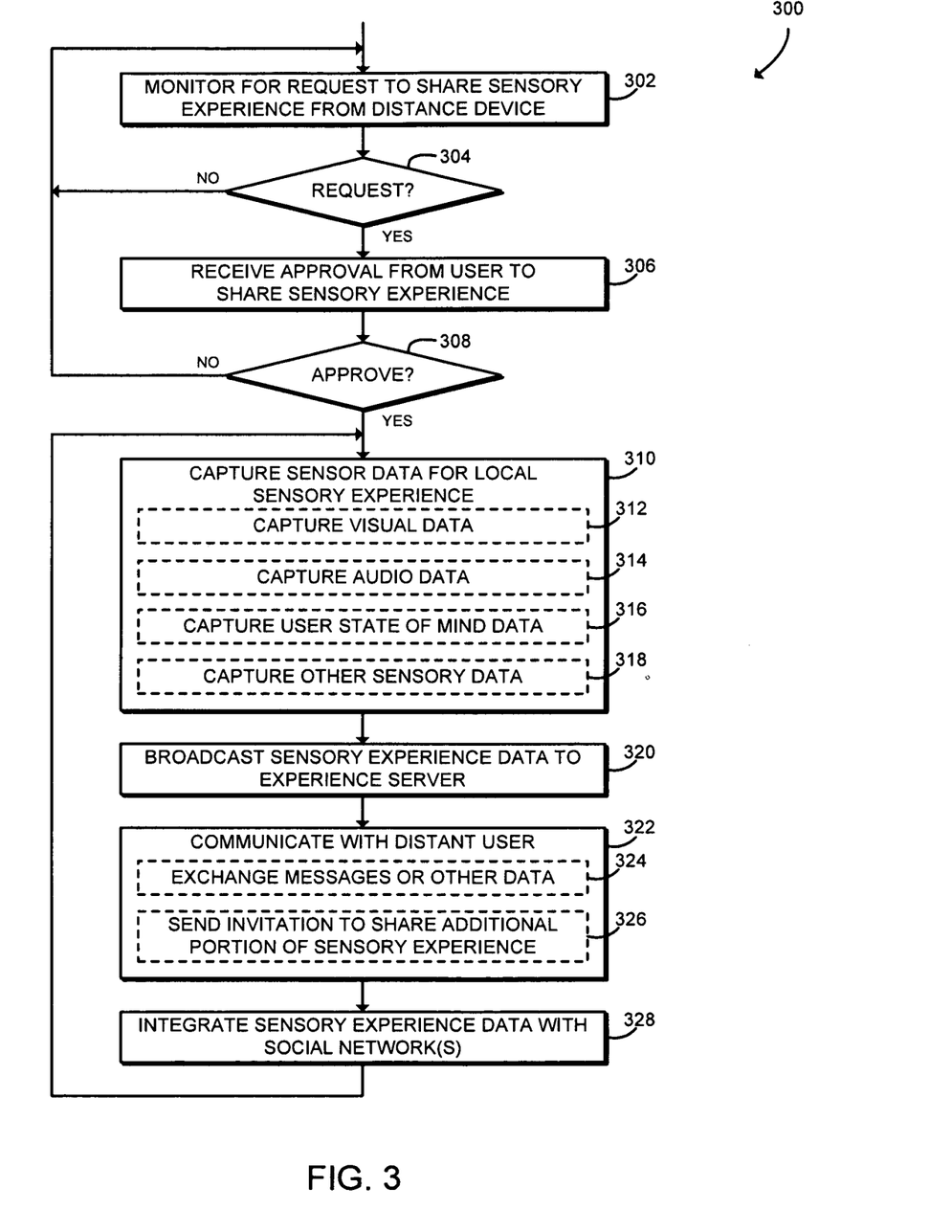
FIG. 3 is a simplified flow diagram of at least one embodiment of a method for collecting and sharing sensory experience information that may be executed by an experience computing device of FIGS. 1 and 2.

Referring now to FIG. 3, in use, an experience computing device 102 may execute a method 300 for collecting and sharing sensory experience information. It should be appreciated that, in some embodiments, the method 300 may be embodied as various instructions stored on a computer-readable media, which may be executed by the processor 120 and/or other components of the experience computing device 102 to cause the experience computing device 102 to perform the method 300. The computer-readable media may be embodied as any type of media capable of being read by the experience computing device 102 including, but not limited to, the memory 124, the data storage device 126, other memory or data storage devices of the experience computing device 102, portable media readable by a peripheral device of the experience computing device 102, and/or other media.

The method 300 begins with block 302, in which the experience computing device 102 monitors for a request to share the local sensory experience from the distance computing device 106. The request may be received, for example, directly from the distance computing device 106 or via the experience server 104. In block 304, the experience computing device 102 determines whether a request has been received. If not, the method 300 loops back to block 302 to continue monitoring for requests. If a request to share the local sensory experience was received, the method 300 advances to block 306.

In block 306, the experience computing device 102 receives approval from a local user to share the sensory experience. For example, the experience computing device 102 may prompt the user for approval using the display 130 and/or the audio device 132, and may receive the approval using one or more user input devices. Requiring local user approval before sharing the local sensory experience may maintain user privacy and/or security. In block 308, the experience computing device 102 determines whether user approval was received. If not, the method 300 loops back to block 302 to continue monitoring for requests to share the sensory experience. If user approval was received, the method 300 advances to block 310.

In block 310, the experience computing device 102 captures sensor data relating to or otherwise indicative of the local sensory experience of the experience computing device 102. The experience computing device 102 may capture sensor data relating to any sense or other experience that may be perceived by a user of the experience computing device 102. As described above, in some embodiments the experience computing device 102 may capture sensor data from the local user's perspective, point of view, and/or location, for example by capturing data from one or more wearable devices or sensors. In some embodiments, the experience computing device 102 may capture sensor data from other perspectives, for example from one or more fixed sensors located in the physical surroundings of the user, or from one or more unmanned aerial vehicles or other mobile devices located in the physical surroundings of the user. In some embodiments, the experience computing device 102 may associate synchronization metadata with the captured sensor data, such as timestamps or other contemporaneous data. As described further below, the synchronization metadata may support aggregating sensor data from multiple experience computing devices 102. Additionally or alternatively, synchronization metadata such as timestamps may support playing back a recorded sensory experience at a later time (i.e., for a distance user who is distance in time).

In some embodiments, in block 312 the experience computing device 102 may capture visual data, for example using the camera 134. In some embodiments, in block 314 the experience computing device 102 may capture audio data, for example using the audio sensor 136. In some embodiments, in block 316, the experience computing device 102 may capture sensor data indicative of the state of mind and/or emotions of one or more local users. For example, the experience computing device 102 may capture sensor data indicative of the language in use, gestures in use, or otherwise indicative of the human emotions and emotional reactions of the user of the experience computing device 102 and/or other attending persons. In some embodiments, in block 318, the experience computing device 102 may capture other sensory data from the sensors 138. For example, the experience computing device 102 may capture sensor data indicative of scents from a chemical sensor 138. As another example, the experience computing device 102 may capture data from a motion sensor 138, a temperature sensor 138, a touch sensor 138 (e.g., touch and/or pressure data), or other sensor data.

In block 320, the experience computing device 102 broadcasts the captured sensory experience data to the experience server 104. As described below in connection with FIGS. 4 and 5, the experience server 104 may analyze the captured sensory experience data and transmit it to the distance computing device 106.

In block 322, the experience computing device 102 may communicate with a distant user of the distance computing device 106. In some embodiments, in block 324, the experience computing device 102 may exchange messages (e.g., text, audio, or video messages) or other data with the distance computing device 106. In some embodiments, in block 326 the experience computing device 102 may send an invitation to share an additional portion of the sensory experience. For example, the experience computing device 102 may share additional sensory experience data, share sensory experience data from additional sensors 138, or otherwise increase the quality and/or quantity of sensory experience shared with the distance computing device 106.

In block 328, the experience computing device 102 may integrate the sensory experience data with one or more social networks. For example, the experience computing device 102 may post one or more images, audio files, or other media to a social network server. After integrating the sensory experience, the method 300 loops back to block 310 to continue capturing sensor data indicative of the local sensory experience.

Figure 4:
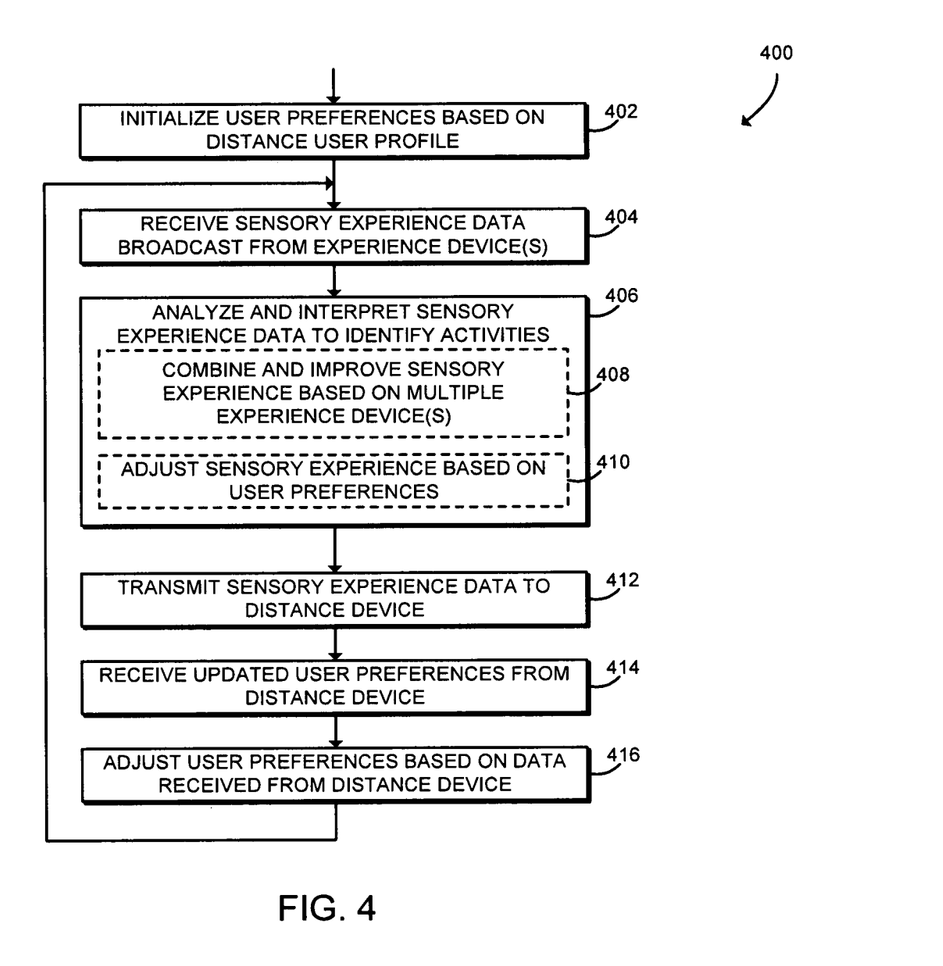
FIG. 4 is a simplified flow diagram of at least one embodiment of a method for analyzing sensory experience information that may be executed by an experience server of FIGS. 1 and 2.

Referring now to FIG. 4, in use, the experience server 104 may execute a method 400 for analyzing sensory experience information. It should be appreciated that, in some embodiments, the method 400 may be embodied as various instructions stored on a computer-readable media, which may be executed by the processor 140 and/or other components of the experience server 104 to cause the experience server 104 to perform the method 400. The computer-readable media may be embodied as any type of media capable of being read by the experience server 104 including, but not limited to, the memory 144, the data storage device 146, other memory or data storage devices of the experience server 104, portable media readable by a peripheral device of the experience server 104, and/or other media.

The method 400 begins with block 402, in which the experience server 104 initializes one or more user preferences based on a user profile of a user of the distance computing device 106. The user preferences may include preferences or other settings related to the amount, quality, intensity, or other characteristics of the sensory experience to be shared to the user. The user profile may include various attributes of the distance user (e.g., age, gender, education, time restrictions, etc.), and may be used to compare the distance user with other users having similar profiles, for example using one or more social media databases. The experience server 104 may configure the user preferences based on the preferences of users with similar profiles.

In block 404, the experience server 104 receives sensory experience data broadcast from one or more experience computing devices 102. As described above in connection with FIG. 3, the sensory experience data is indicative of the local sensory experience of the user of each experience computing device 102. The sensory experience data may be captured by the camera 134, the audio sensor 136, and/or the other sensors 138 of each experience computing device 102.

In block 406, the experience server 104 analyzes and interprets the sensory experience data to identify one or more activities associated with the local sensory experience. For example, the experience server 104 may analyze audio and/or video data to determine the local sensory experiences of the experience computing devices 102 are associated with a concert. As another example, the experience server 104 may analyze touch sensor data to determine that the users of the experience computing devices 102 are in contact (e.g., a group hug). The experience server 104 may also determine the identity, presence, emotions, or other characteristics of persons attending the event. In some embodiments, in block 408, the experience server 104 may combine and improve the sensory experience data based on data received from multiple experience computing devices 102. For example, the experience server 104 may combine or otherwise synthesize sensory experience data to generate data with enhanced coverage of the event (e.g., multiple viewpoints), data with increased fidelity, or otherwise improved data. The experience server 104 may use synchronization metadata such as timestamps associated with the sensory experience data to aggregate the sensory experience data received from multiple experience computing devices 102. Thus, increasing the number of experience computing devices 102 may allow the experience server 104 to improve the combined sensory experience data. Additionally or alternatively, in some embodiments the experience server 104 may support searching across the sensory experience data based on the sensory experience data itself and/or associated metadata. For example, in some embodiments, the experience server 104 may search for exiting sections of the sensory experience data based on the heart rate data of specific user(s) or measured across all users.

In some embodiments, in block 410 the experience server 104 may control the generation of combined sensory experience data based on the user preferences. For example, the experience server 104 may adjust an intensity, quality, or other characteristics of the sensory experience data based on the user preferences. In some embodiments, the experience server 104 may select sensory experience data from several available experience computing devices 102 based on the user preferences, for example selecting certain points of view or areas of focus.

In block 412, the experience server 104 transmits the sensory experience data to the distance computing device 106. As described further below in connection with FIG. 5, the distance computing device 106 may render a sensory experience for the distance user based on the combined sensory experience data.

In block 414, the experience server 104 may receive one or more updated user preferences from the distance computing device 106. As described above in connection with block 402, the user preferences may include preferences or other settings related to the amount, quality, intensity, or other characteristics of the sensory experience to be shared to the user. For example, the user preferences may include a desired volume setting for audio data. In block 416, the experience server 104 may adjust the user preferences based on the updated user preferences received from the distance computing device 106. As described above in connection with block 410, the adjusted user preferences may allow the experience server 104 to control the sensory experience data provided to the distance computing device 106. For example, the volume, intensity, quality, or other characteristics of the sensory experience data may be adjusted based on the preferences received from the distance computing device 106. After adjusting the user preferences, the method 400 loops back to block 404 to continue receiving sensory experience data.

Figure 5:
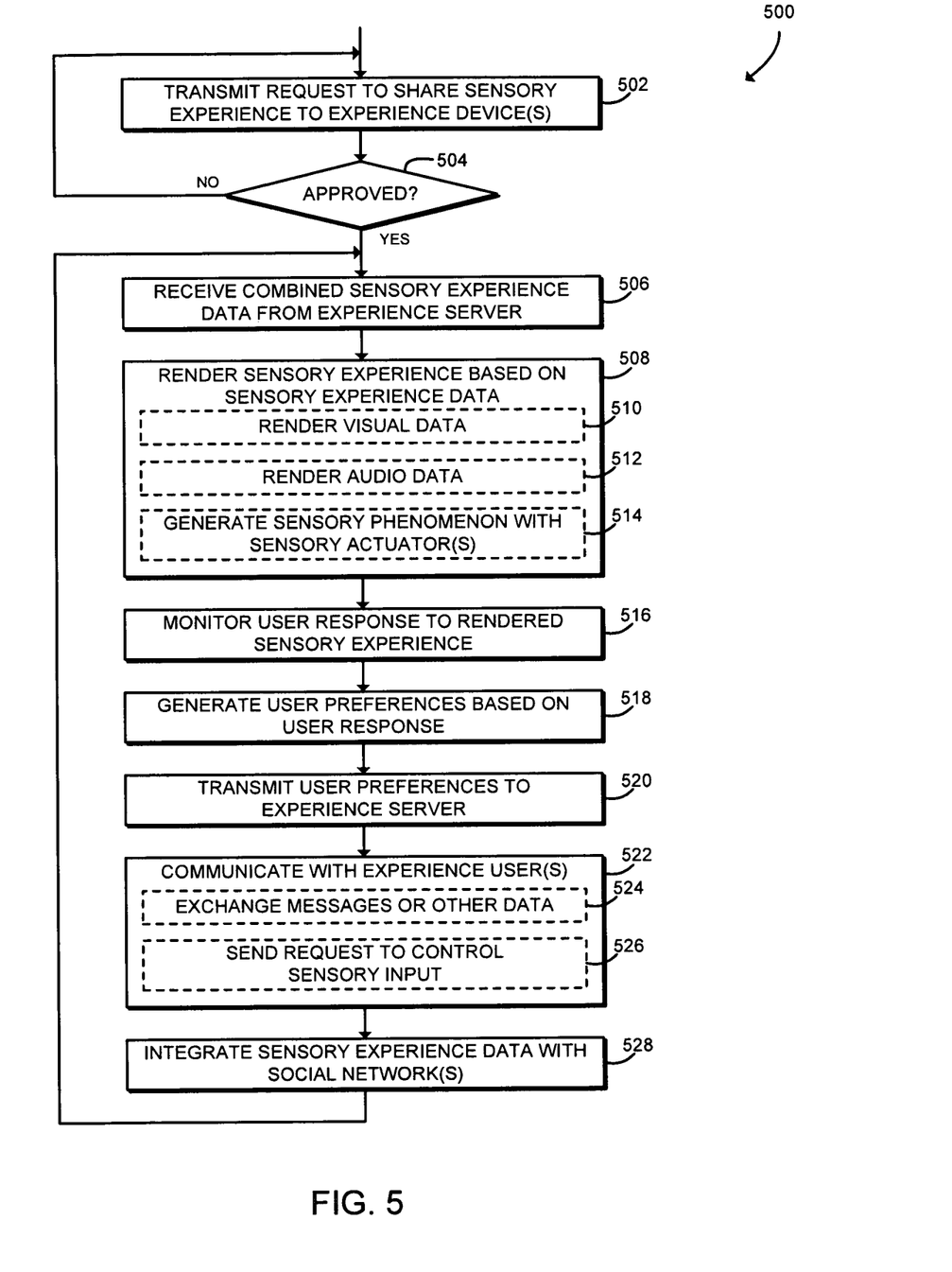
FIG. 5 is a simplified flow diagram of at least one embodiment of a method for rendering sensory experience information that may be executed by a distance computing device of FIGS. 1 and 2.

Referring now to FIG. 5, in use, the distance computing device 106 may execute a method 500 for rendering sensory experience information. It should be appreciated that, in some embodiments, the method 500 may be embodied as various instructions stored on a computer-readable media, which may be executed by the processor 160 and/or other components of the distance computing device 106 to cause the distance computing device 106 to perform the method 500. The computer-readable media may be embodied as any type of media capable of being read by the distance computing device 106 including, but not limited to, the memory 164, the data storage device 166, other memory or data storage devices of the distance computing device 106, portable media readable by a peripheral device of the distance computing device 106, and/or other media.

The method 500 begins with block 502, in which the distance computing device 106 transmits a request to share sensory experience to one or more experience computing devices 102. The request may be transmitted directly to the experience computing devices 102, or may be transmitted via the experience server 104. In some embodiments, the distance computing device 106 may request to share the sensory experience of his or her friends or other known users. Additionally or alternatively, the distance computing device 106 may request to share the sensory experience of other users of the experience server 104. In block 504, the distance computing device 106 determines whether the request to share sensory experience was approved by the user of the experience computing device 102. If not, the method 500 loops back to block 502 to make additional requests. If the request was approved, the method 500 advances to block 506.

In block 506, the distance computing device 106 receives combined sensory experience data from the experience server 104. As described above in connection with FIGS. 3 and 4, the sensory experience data is indicative of the local sensory experience captured by each experience computing device 102. The sensory experience data may be captured by the camera 134, the audio sensor 136, and/or the other sensors 138 of each experience computing device 102.

In block 508, the distance computing device 106 renders a sensory experience based on the sensory experience data. The distance computing device 106 may use any technique to render the sensory experience based on the sensory experience data. In some embodiments, in block 510, the distance computing device 106 may render visual data, for example using the display 130. In some embodiments, in block 512, the distance computing device 106 may render audio data, for example using the audio device 132. In some embodiments, in block 514, the distance computing device 106 may generate a sensory phenomenon using one or more of the sensory actuators 180 of the distance computing device 106. For example, the distance computing device 106 may generate a haptic phenomenon (e.g., force, pressure, or other tactile sensation) using a haptic feedback actuator 180. In that example, in response to the experience server 104 determining that the users of the experience computing devices 102 are engaged in a group hug, the distance computing device 106 may activate one or more sensory actuators 180 to render the sensation of a group hug. As another example, the distance computing device 106 may generate a scent (e.g., emit one or more chemicals) using an odor-generating device 180. In some embodiments, the distance computing device 106 may generate a sensory phenomenon that is representative of but is not the same as the sensory experience measured by the experience computing devices 102 (e.g., cross-modal or inter-modal representation). For example, the feeling of loud bass music in a user's chest at a concert may be represented with haptic feedback, such as a rhythmic squeezing sensation (e.g., of an upper arm) by a haptic cuff or other garment. As another example, light or sound originating from behind a user may also be represented with haptic feedback, such as a tapping sensation on the back of the user's shoulder, head, or other location.

In block 516, the distance computing device 106 monitors the distance user's response to the rendered sensory experience. The distance computing device 106 may monitor the user response using one or more sensors 178, including monitoring biometric feedback data. The distance computing device 106 may monitor the user's physical response or state of mind (e.g., interest or non-interest). For example, the distance computing device 106 may use one or more sensors 178 to monitor the distance user's pupil dilation, which may be indicative of the distance user's state of mind.

In block 518, the distance computing device 106 may generate one or more user preferences based on the user response. The user preferences may indicate whether to increase or decrease the intensity of the sensory experience. For example, if the user response indicates that the user has lost interest, user preferences may be generated to increase the intensity of the sensory experience. In block 520, the distance computing device 106 transmits the user preferences to the experience server 104. As described above in connection with FIG. 4, the experience server 104 may adjust the sensory experience data based on the user preferences.

In block 522, the distance computing device 106 may communicate with one or more users of the experience computing devices 102. In some embodiments, in block 524, the distance computing device 106 may exchange messages (e.g., text, audio, or video messages) or other data with an experience computing device 102. In some embodiments, in block 526 the distance computing device 106 may send a request to control the sensory input of an experience computing device 102. For example, the distance computing device 106 may request that an experience computing device 102 focus the camera 134, the audio sensor 136, and/or other sensors 138 on a particular location or otherwise direct the capture of sensory input by the experience computing device 102.

In block 528, the distance computing device 106 may integrate the sensory experience data with one or more social networks. For example, the distance computing device 106 may post one or more images, audio files, or other media to a social network server. After integrating the sensory experience, the method 500 loops back to block 506 to continue rendering the sensory experience.

EXAMPLES

Illustrative examples of the technologies disclosed herein are provided below. An embodiment of the technologies may include any one or more, and any combination of, the examples described below.

Example 1 includes a computing device for sensory experience sharing, the computing device comprising: a crowdsourcing aggregation module to receive sensor data from a plurality of experience computing devices, wherein the sensor data is indicative of a local sensory experience associated with each of the experience computing devices; an experience analysis module to analyze the sensor data to generate combined sensory experience data, wherein the combined sensory experience data is indicative of the local sensory experiences associated with the experience computing devices; and a distance module to transmit the combined sensory experience data to a distance computing device, wherein the distance computing device is distant from the plurality of experience computing devices.

Example 2 includes the subject matter of Example 1, and wherein to analyze the sensor data comprises to identify an activity associated with the local sensory experiences based on the sensor data.

Example 3 includes the subject matter of any of Examples 1 and 2, and wherein the sensor data comprises visual data or audio data.

Example 4 includes the subject matter of any of Examples 1-3, and wherein the sensor data comprises sensor data indicative of a state of mind of an experience user associated with the experience computing device.

Example 5 includes the subject matter of any of Examples 1-4, and wherein the sensor data indicative of the state of mind of the experience user comprises data indicative of language in use by the experience user, gestures performed by the experience user, or emotional state of the experience user.

Example 6 includes the subject matter of any of Examples 1-5, and wherein the sensor data comprises chemical sensor data, motion sensor data, temperature sensor data, or touch sensor data.

Example 7 includes the subject matter of any of Examples 1-6, and wherein the distance module is further to adjust the combined sensory experience data based on user preferences associated with a user of the distance computing device.

Example 8 includes the subject matter of any of Examples 1-7, and further comprising an initial settings module to initialize the user preferences based on a profile of the user of the distance computing device.

Example 9 includes the subject matter of any of Examples 1-8, and wherein the distance module is further to receive the user preferences from the distance computing device in response to transmission of the combined sensory experience data to the distance computing device.

Example 10 includes the subject matter of any of Examples 1-9, and wherein to receive the user preferences from the distance computing device comprises to receive sensor data indicative of a user response of a distance user of the distance computing device.

Example 11 includes the subject matter of any of Examples 1-10, and further comprising an experience enhancement module to receive an invitation from a first experience computing device to receive additional sensor data indicative of the local sensory experience, wherein to analyze the sensor data to generate the combined sensory experience data comprises to enhance sensor data received from the first experience computing device in response to receipt of the invitation from the first experience computing device.

Example 12 includes a computing device for sensory experience sharing, the computing device comprising: an experience module to receive combined sensory experience data from an experience server, wherein the combined sensory experience data is indicative of a local sensory experience associated with each of a plurality of experience computing devices distant from the computing device; and a sensory output module to render a sensory experience based on the combined sensory experience data.

Example 13 includes the subject matter of Example 12, and wherein: the experience module is further to transmit a request to share the local sensory experience to the experience server, wherein to receive the combined sensory experience data comprises to receive the combined sensory experience data in response to transmission of the request to share the local sensory experience.

Example 14 includes the subject matter of any of Examples 12 and 13, and wherein to render the sensory experience based on the combined sensory experience data comprises to render visual data or audio data.

Example 15 includes the subject matter of any of Examples 12-14, and wherein to render the sensory experience based on the combined sensory experience data comprises to generate a sensory phenomenon with a sensory actuator of the computing device.

Example 16 includes the subject matter of any of Examples 12-15, and wherein to generate the sensory phenomenon with the sensory actuator of the computing device comprises to generate a haptic phenomenon.

Example 17 includes the subject matter of any of Examples 12-16, and wherein to generate the sensory phenomenon with the sensory actuator of the computing device comprises to generate a scent.

Example 18 includes the subject matter of any of Examples 12-17, and further comprising an experience alteration module to monitor sensor data indicative of a user response of a local user in response to rendering of the sensory experience.

Example 19 includes the subject matter of any of Examples 12-18, and wherein the sensor data comprises biometric feedback data associated with the local user.

Example 20 includes the subject matter of any of Examples 12-19, and wherein the sensor data comprises sensor data indicative of a state of mind of the local user.

Example 21 includes the subject matter of any of Examples 12-20, and wherein the experience alteration module is further to: generate user preferences based on the sensor data indicative of the user response; and transmit the user preferences to the experience server.

Example 22 includes the subject matter of any of Examples 12-21, and further comprising a user interface module to communicate with a first experience computing device of the plurality of experience computing devices.

Example 23 includes the subject matter of any of Examples 12-22, and wherein to communicate with the first experience computing device comprises to exchange a text message, an audio message, or a video message.

Example 24 includes the subject matter of any of Examples 12-23, and wherein to communicate with the first experience computing device comprises to transmit a request to control sensory input of the first experience computing device.

Example 25 includes the subject matter of any of Examples 12-24, and further comprising a social module to publish the combined sensory experience data to a social media server.

Example 26 includes a computing device for sensory experience sharing, the computing device comprising: an authorization module to (i) receive a request to share a local sensory experience and (ii) receive approval from a local user to share the local sensory experience in response to receipt of the request to share the local sensory experience; and a sensory module to (i) capture sensor data indicative of the local sensory experience from one or more sensors of the computing device in response to receipt of the approval from the local user and (ii) transmit the sensor data to an experience server.

Example 27 includes the subject matter of Example 26, and wherein the sensor data comprises visual data or audio data.

Example 28 includes the subject matter of any of Examples 26 and 27, and wherein the sensor data comprises sensor data indicative of a state of mind of a local user.

Example 29 includes the subject matter of any of Examples 26-28, and wherein the sensor data indicative of the state of mind of the user comprises sensor data indicative of language in use by the local user, gestures performed by the local user, or an emotional state of the local user.

Example 30 includes the subject matter of any of Examples 26-29, and wherein the one or more sensors of the computing device comprise a sensor selected from a chemical sensor, a motion sensor, a temperature sensor, or a touch sensor.

Example 31 includes the subject matter of any of Examples 26-30, and further comprising a user interface module to communicate with a distance computing device, wherein the distance computing device shares the local sensory experience via the experience server.

Example 32 includes the subject matter of any of Examples 26-31, and wherein to communicate with the distance computing device comprises to exchange a text message, an audio message, or a video message.

Example 33 includes the subject matter of any of Examples 26-32, and wherein to communicate with the distance computing device comprises to invite the distance computing device to receive additional sensor data indicative of the local sensory experience.

Example 34 includes the subject matter of any of Examples 26-33, and further comprising a social module to publish the sensor data indicative of the local sensory experience to a social media server.

Example 35 includes a method for sensory experience sharing, the method comprising: receiving, by a computing device, sensor data from a plurality of experience computing devices, wherein the sensor data is indicative of a local sensory experience associated with each of the experience computing devices; analyzing, by the computing device, the sensor data to generate combined sensory experience data, wherein the combined sensory experience data is indicative of the local sensory experiences associated with the experience computing devices; and transmitting, by the computing device, the combined sensory experience data to a distance computing device, wherein the distance computing device is distant from the plurality of experience computing devices.

Example 36 includes the subject matter of Example 35, and wherein analyzing the sensor data comprises identifying an activity associated with the local sensory experiences based on the sensor data.

Example 37 includes the subject matter of any of Examples 35 and 36, and wherein receiving the sensor data from the plurality of experience computing devices comprises receiving visual data or audio data.

Example 38 includes the subject matter of any of Examples 35-37, and wherein receiving the sensor data from the plurality of experience computing devices comprises receiving sensor data indicative of a state of mind of an experience user associated with the experience computing device.

Example 39 includes the subject matter of any of Examples 35-38, and wherein receiving the sensor data indicative of the state of mind of the experience user comprises receiving data indicative of language in use by the experience user, gestures performed by the experience user, or emotional state of the experience user.

Example 40 includes the subject matter of any of Examples 35-39, and wherein receiving the sensor data from the plurality of experience computing devices comprises receiving chemical sensor data, motion sensor data, temperature sensor data, or touch sensor data.

Example 41 includes the subject matter of any of Examples 35-40, and further comprising adjusting, by the computing device, the combined sensory experience data based on user preferences associated with a user of the distance computing device.

Example 42 includes the subject matter of any of Examples 35-41, and further comprising initializing, by the computing device, the user preferences based on a profile of the user of the distance computing device.

Example 43 includes the subject matter of any of Examples 35-42, and further comprising receiving, by the computing device, the user preferences from the distance computing device in response to transmitting the combined sensory experience data to the distance computing device.

Example 44 includes the subject matter of any of Examples 35-43, and wherein receiving the user preferences from the distance computing device comprises receiving sensor data indicative of a user response of a distance user of the distance computing device.

Example 45 includes the subject matter of any of Examples 35-44, and further comprising: receiving, by the computing device, an invitation from a first experience computing device to receive additional sensor data indicative of the local sensory experience; wherein analyzing the sensor data to generate the combined sensory experience data comprises enhancing sensor data received from the first experience computing device in response to receiving the invitation from the first experience computing device.

Example 46 includes a method for sensory experience sharing, the method comprising: receiving, by a computing device, combined sensory experience data from an experience server, wherein the combined sensory experience data is indicative of a local sensory experience associated with each of a plurality of experience computing devices distant from the computing device; and rendering, by the computing device, a sensory experience based on the combined sensory experience data.

Example 47 includes the subject matter of Example 46, and further comprising: transmitting, by the computing device, a request to share the local sensory experience to the experience server, wherein receiving the combined sensory experience data comprises receiving the combined sensory experience data in response to transmitting the request to share the local sensory experience.

Example 48 includes the subject matter of any of Examples 46 and 47, and wherein rendering the sensory experience based on the combined sensory experience data comprises rendering visual data or audio data.

Example 49 includes the subject matter of any of Examples 46-48, and wherein rendering the sensory experience based on the combined sensory experience data comprises generating a sensory phenomenon with a sensory actuator of the computing device.

Example 50 includes the subject matter of any of Examples 46-49, and wherein generating the sensory phenomenon with the sensory actuator of the computing device comprises generating a haptic phenomenon.

Example 51 includes the subject matter of any of Examples 46-50, and wherein generating the sensory phenomenon with the sensory actuator of the computing device comprises generating a scent.

Example 52 includes the subject matter of any of Examples 46-51, and further comprising monitoring, by the computing device, sensor data indicative of a user response of a local user in response to rendering the sensory experience.

Example 53 includes the subject matter of any of Examples 46-52, and wherein monitoring the sensor data comprises monitoring biometric feedback data associated with the local user.

Example 54 includes the subject matter of any of Examples 46-53, and wherein monitoring the sensor data comprises monitoring sensor data indicative of a state of mind of the local user.

Example 55 includes the subject matter of any of Examples 46-54, and further comprising: generating, by the computing device, user preferences based on the sensor data indicative of the user response; and transmitting, by the computing device, the user preferences to the experience server.

Example 56 includes the subject matter of any of Examples 46-55, and further comprising communicating, by the computing device, with a first experience computing device of the plurality of experience computing devices.

Example 57 includes the subject matter of any of Examples 46-56, and wherein communicating with the first experience computing device comprises exchanging a text message, an audio message, or a video message.

Example 58 includes the subject matter of any of Examples 46-57, and wherein communicating with the first experience computing device comprises transmitting a request to control sensory input of the first experience computing device.

Example 59 includes the subject matter of any of Examples 46-58, and further comprising publishing, by the computing device, the combined sensory experience data to a social media server.

Example 60 includes a method for sensory experience sharing, the method comprising: receiving, by a computing device, a request to share a local sensory experience; and receiving, by the computing device, approval from a local user to share the local sensory experience in response to receiving the request to share the local sensory experience; capturing, by the computing device, sensor data indicative of the local sensory experience from one or more sensors of the computing device in response to receiving the approval from the local user; and transmitting, by the computing device, the sensor data to an experience server.

Example 61 includes the subject matter of Example 60, and wherein capturing the sensor data comprises capturing visual data or audio data.

Example 62 includes the subject matter of any of Examples 60 and 61, and wherein capturing the sensor data comprises capturing sensor data indicative of a state of mind of a local user.

Example 63 includes the subject matter of any of Examples 60-62, and wherein capturing the sensor data indicative of the state of mind of the user comprises capturing sensor data indicative of language in use by the local user, gestures performed by the local user, or an emotional state of the local user.

Example 64 includes the subject matter of any of Examples 60-63, and wherein capturing the sensor data comprises capturing sensor data from a chemical sensor, a motion sensor, a temperature sensor, or a touch sensor.

Example 65 includes the subject matter of any of Examples 60-64, and further comprising communicating, by the computing device, with a distance computing device, wherein the distance computing device shares the local sensory experience via the experience server.

Example 66 includes the subject matter of any of Examples 60-65, and wherein communicating with the distance computing device comprises exchanging a text message, an audio message, or a video message.

Example 67 includes the subject matter of any of Examples 60-66, and wherein communicating with the distance computing device comprises inviting the distance computing device to receive additional sensor data indicative of the local sensory experience.

Example 68 includes the subject matter of any of Examples 60-67, and further comprising publishing, by the computing device, the sensor data indicative of the local sensory experience to a social media server.

Example 69 includes a computing device comprising: a processor; and a memory having stored therein a plurality of instructions that when executed by the processor cause the computing device to perform the method of any of Examples 35-68.

Example 70 includes one or more machine readable storage media comprising a plurality of instructions stored thereon that in response to being executed result in a computing device performing the method of any of Examples 35-68.

Example 71 includes a computing device comprising means for performing the method of any of Examples 35-68.

Example 72 includes a computing device for sensory experience sharing, the computing device comprising: means for receiving sensor data from a plurality of experience computing devices, wherein the sensor data is indicative of a local sensory experience associated with each of the experience computing devices; means for analyzing the sensor data to generate combined sensory experience data, wherein the combined sensory experience data is indicative of the local sensory experiences associated with the experience computing devices; and means for transmitting the combined sensory experience data to a distance computing device, wherein the distance computing device is distant from the plurality of experience computing devices.

Example 73 includes the subject matter of Example 72, and wherein the means for analyzing the sensor data comprises means for identifying an activity associated with the local sensory experiences based on the sensor data.

Example 74 includes the subject matter of any of Examples 72 and 73, and wherein the means for receiving the sensor data from the plurality of experience computing devices comprises means for receiving visual data or audio data.

Example 75 includes the subject matter of any of Examples 72-74, and wherein the means for receiving the sensor data from the plurality of experience computing devices comprises means for receiving sensor data indicative of a state of mind of an experience user associated with the experience computing device.

Example 76 includes the subject matter of any of Examples 72-75, and wherein the means for receiving the sensor data indicative of the state of mind of the experience user comprises means for receiving data indicative of language in use by the experience user, gestures performed by the experience user, or emotional state of the experience user.

Example 77 includes the subject matter of any of Examples 72-76, and wherein the means for receiving the sensor data from the plurality of experience computing devices comprises means for receiving chemical sensor data, motion sensor data, temperature sensor data, or touch sensor data.

Example 78 includes the subject matter of any of Examples 72-77, and further comprising means for adjusting the combined sensory experience data based on user preferences associated with a user of the distance computing device.

Example 79 includes the subject matter of any of Examples 72-78, and further comprising means for initializing the user preferences based on a profile of the user of the distance computing device.

Example 80 includes the subject matter of any of Examples 72-79, and further comprising means for receiving the user preferences from the distance computing device in response to transmitting the combined sensory experience data to the distance computing device.

Example 81 includes the subject matter of any of Examples 72-80, and wherein the means for receiving the user preferences from the distance computing device comprises means for receiving sensor data indicative of a user response of a distance user of the distance computing device.

Example 82 includes the subject matter of any of Examples 72-81, and further comprising: means for receiving an invitation from a first experience computing device to receive additional sensor data indicative of the local sensory experience; wherein the means for analyzing the sensor data to generate the combined sensory experience data comprises means for enhancing sensor data received from the first experience computing device in response to receiving the invitation from the first experience computing device.

Example 83 includes a computing device for sensory experience sharing, the computing device comprising: means for receiving combined sensory experience data from an experience server, wherein the combined sensory experience data is indicative of a local sensory experience associated with each of a plurality of experience computing devices distant from the computing device; and means for rendering a sensory experience based on the combined sensory experience data.

Example 84 includes the subject matter of Example 83, and further comprising: means for transmitting a request to share the local sensory experience to the experience server, wherein the means for receiving the combined sensory experience data comprises means for receiving the combined sensory experience data in response to transmitting the request to share the local sensory experience.

Example 85 includes the subject matter of any of Examples 83 and 84, and wherein the means for rendering the sensory experience based on the combined sensory experience data comprises means for rendering visual data or audio data.

Example 86 includes the subject matter of any of Examples 83-85, and wherein the means for rendering the sensory experience based on the combined sensory experience data comprises means for generating a sensory phenomenon with a sensory actuator of the computing device.

Example 87 includes the subject matter of any of Examples 83-86, and wherein the means for generating the sensory phenomenon with the sensory actuator of the computing device comprises means for generating a haptic phenomenon.

Example 88 includes the subject matter of any of Examples 83-87, and wherein the means for generating the sensory phenomenon with the sensory actuator of the computing device comprises means for generating a scent.

Example 89 includes the subject matter of any of Examples 83-88, and further comprising means for monitoring sensor data indicative of a user response of a local user in response to rendering the sensory experience.

Example 90 includes the subject matter of any of Examples 83-89, and wherein the means for monitoring the sensor data comprises means for monitoring biometric feedback data associated with the local user.

Example 91 includes the subject matter of any of Examples 83-90, and wherein the means for monitoring the sensor data comprises means for monitoring sensor data indicative of a state of mind of the local user.

Example 92 includes the subject matter of any of Examples 83-91, and further comprising: means for generating user preferences based on the sensor data indicative of the user response; and means for transmitting the user preferences to the experience server.

Example 93 includes the subject matter of any of Examples 83-92, and further comprising means for communicating with a first experience computing device of the plurality of experience computing devices.

Example 94 includes the subject matter of any of Examples 83-93, and wherein the means for communicating with the first experience computing device comprises means for exchanging a text message, an audio message, or a video message.

Example 95 includes the subject matter of any of Examples 83-94, and wherein the means for communicating with the first experience computing device comprises means for transmitting a request to control sensory input of the first experience computing device.

Example 96 includes the subject matter of any of Examples 83-95, and further comprising means for publishing the combined sensory experience data to a social media server.

Example 97 includes a computing device for sensory experience sharing, the computing device comprising: means for receiving a request to share a local sensory experience; and means for receiving approval from a local user to share the local sensory experience in response to receiving the request to share the local sensory experience; means for capturing sensor data indicative of the local sensory experience from one or more sensors of the computing device in response to receiving the approval from the local user; and means for transmitting the sensor data to an experience server.

Example 98 includes the subject matter of Example 97, and wherein the means for capturing the sensor data comprises means for capturing visual data or audio data.

Example 99 includes the subject matter of any of Examples 97 and 98, and wherein the means for capturing the sensor data comprises means for capturing sensor data indicative of a state of mind of a local user.

Example 100 includes the subject matter of any of Examples 97-99, and wherein the means for capturing the sensor data indicative of the state of mind of the user comprises means for capturing sensor data indicative of language in use by the local user, gestures performed by the local user, or an emotional state of the local user.

Example 101 includes the subject matter of any of Examples 97-100, and wherein the means for capturing the sensor data comprises means for capturing sensor data from a chemical sensor, a motion sensor, a temperature sensor, or a touch sensor.

Example 102 includes the subject matter of any of Examples 97-101, and further comprising means for communicating with a distance computing device, wherein the distance computing device shares the local sensory experience via the experience server.

Example 103 includes the subject matter of any of Examples 97-102, and wherein the means for communicating with the distance computing device comprises means for exchanging a text message, an audio message, or a video message.

Example 104 includes the subject matter of any of Examples 97-103, and wherein the means for communicating with the distance computing device comprises means for inviting the distance computing device to receive additional sensor data indicative of the local sensory experience.

Example 105 includes the subject matter of any of Examples 97-104, and further comprising means for publishing the sensor data indicative of the local sensory experience to a social media server.

The invention claimed is:

1. A computing device for sensory experience sharing, the computing device comprising:
   a crowdsourcing aggregation module to receive sensor data from a plurality of experience computing devices, wherein the sensor data is indicative of a local sensory experience associated with each of the experience computing devices, and wherein the sensor data received from a first experience computing device of the plurality of experience computing devices is captured by the first experience computing device from an unmanned aerial vehicle;
   an initial settings module to initialize one or more user preferences associated with a user of the distance computing device based on a search of one or more social media databases for user preferences of other users meeting one or more demographic attributes of the user of the distance computing device;
   an experience analysis module to analyze the sensor data to generate combined sensory experience data, wherein the combined sensory experience data is indicative of the local sensory experiences associated with the experience computing devices; and
   a distance module to (i) transmit the combined sensory experience data to a distance computing device, wherein the distance computing device is distant from the plurality of experience computing devices, (ii) receive user preferences associated with the user of the distance computing device from the distance computing device in response to transmission of the combined sensory experience data to the distance computing device, wherein the user preferences are based on biometric feedback data associated with the user of the distance computing device that is indicative of a physical response of the user of the distance computing device, wherein the physical response is indicative of a state of mind of the user of the distance computing device, and (iii) adjust the combined sensory experience data based on the user preferences.

2. The computing device of claim 1, wherein to analyze the sensor data comprises to identify an activity associated with the local sensory experiences based on the sensor data.

3. The computing device of claim 1, wherein the sensor data comprises visual data or audio data.

4. The computing device of claim 1, wherein the sensor data comprises sensor data indicative of a state of mind of an experience user associated with the experience computing device.

5. The computing device of claim 1, wherein the sensor data comprises chemical sensor data, motion sensor data, temperature sensor data, or touch sensor data.

6. One or more non-transitory, machine readable storage media comprising a plurality of instructions that in response to being executed cause a computing device to:

receive sensor data from a plurality of experience computing devices, wherein the sensor data is indicative of a local sensory experience associated with each of the experience computing devices, and wherein the sensor data received from a first experience computing device of the plurality of experience computing devices is captured by the first experience computing device from an unmanned aerial vehicle;

initialize one or more user preferences associated with a user of the distance computing device based on a search of one or more social media databases for user preferences of other users meeting one or more demographic attributes of the user of the distance computing device;

analyze the sensor data to generate combined sensory experience data, wherein the combined sensory experience data is indicative of the local sensory experiences associated with the experience computing devices;

transmit the combined sensory experience data to a distance computing device, wherein the distance computing device is distant from the plurality of experience computing devices;

receive user preferences associated with the user of the distance computing device from the distance computing device in response to transmitting the combined sensory experience data to the distance computing device, wherein the user preferences are based on biometric feedback data associated with the user of the distance computing device that is indicative of a physical response of the user of the distance computing device, wherein the physical response is indicative of a state of mind of the user of the distance computing device; and adjust the combined sensory experience data based on the user preferences.

7. The one or more non-transitory, machine readable storage media of claim 6, wherein to analyze the sensor data comprises to identify an activity associated with the local sensory experiences based on the sensor data.

8. The one or more non-transitory, machine readable storage media of claim 6, wherein to receive the sensor data from the plurality of experience computing devices comprises to receive visual data or audio data.

9. A computing device for sensory experience sharing, the computing device comprising:

an experience module to receive combined sensory experience data from an experience server, wherein the combined sensory experience data is indicative of a local sensory experience associated with each of a plurality of experience computing devices distant from the computing device, and wherein the combined sensory experience data is indicative of sensor data received by an experience computing device from an unmanned aerial vehicle;

an initial settings module to initialize one or more user preferences associated with a local user based on a search of one or more social media databases for user preferences of other users meeting one or more demographic attributes of the local user;

a sensory output module to render a sensory experience based on the combined sensory experience data; and an experience alteration module to (i) monitor sensor data indicative of a user physical response of the local user in response to rendering of the sensory experience, wherein the sensor data comprises biometric feedback data associated with the local user and wherein the sensor data is indicative of a state of mind of the local user, (ii) generate user preferences based on the sensor data indicative of the user physical response, and (iii) transmit the user preferences to the experience server.

10. The computing device of claim 9, wherein to render the sensory experience based on the combined sensory experience data comprises to generate a sensory phenomenon with a sensory actuator of the computing device.

11. The computing device of claim 10, wherein to generate the sensory phenomenon with the sensory actuator of the computing device comprises to generate a haptic phenomenon.

12. The computing device of claim 9, further comprising a user interface module to communicate with a first experience computing device of the plurality of experience computing devices.

13. The computing device of claim 12, wherein to communicate with the first experience computing device comprises to transmit a request to control sensory input of the first experience computing device.

14. One or more non-transitory, machine readable storage media comprising a plurality of instructions that in response to being executed cause a computing device to:

receive combined sensory experience data from an experience server, wherein the combined sensory experience data is indicative of a local sensory experience associated with each of a plurality of experience computing devices distant from the computing device, and wherein the combined sensory experience data is indicative of sensor data received by an experience computing device from an unmanned aerial vehicle;

initialize one or more user preferences associated with a local user based on a search of one or more social media databases for user preferences of other users meeting one or more demographic attributes of the local user;

render a sensory experience based on the combined sensory experience data;

monitor sensor data indicative of a user physical response of the local user in response to rendering the sensory experience, wherein the sensor data comprises biometric feedback data associated with the local user and wherein the sensor data is indicative of a state of mind of the local user;

generate user preferences based on the sensor data indicative of the user physical response; and transmit the user preferences to the experience server.

15. The one or more non-transitory, machine readable storage media of claim 14, wherein to render the sensory experience based on the combined sensory experience data comprises to generate a sensory phenomenon with a sensory actuator of the computing device.

16. The one or more non-transitory, machine readable storage media of claim 15, wherein to generate the sensory phenomenon with the sensory actuator of the computing device comprises to generate a haptic phenomenon.

* * * * *